US00PP31134P2

(12) United States Plant Patent
Koppe

(10) Patent No.: US PP31,134 P2
(45) Date of Patent: Nov. 26, 2019

(54) ***BEGONIA* PLANT NAMED 'KRVALWH02'**

(50) Latin Name: *Begonia x hiemalis*
Varietal Denomination: KRVALWH02

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/350,338

(22) Filed: Nov. 2, 2018

(51) Int. Cl.
*A01H 5/02* (2018.01)
*A01H 6/18* (2018.01)

(52) U.S. Cl.
USPC ..... Plt./344

(58) Field of Classification Search
USPC ..... Plt./344

CPC ..... A01H 5/02; A01H 6/18
See application file for complete search history.

(56) References Cited

PUBLICATIONS

PLUTO Plant VAriety Database Jun. 1, 2019.*

* cited by examiner

*Primary Examiner* — Annette H Para
(74) *Attorney, Agent, or Firm* — C. A. Whealy

(57) ABSTRACT

A new and distinct cultivar of *Begonia* plant named 'KRVALWH02' characterized by its upright to outwardly spreading and mounded plant habit; moderately vigorous growth habit; freely branching habit; dark green-colored leaves; freely flowering habit; double-type flowers that are white and yellow in color and held above and beyond the foliar plane; and excellent postproduction longevity.

2 Drawing Sheets

Botanical designation: *Begonia* x *hiemalis*.
Cultivar denomination: 'KRVALWH02'.

BACKGROUND OF THE INVENTION

The present invention relates to a new and distinct cultivar of *Begonia* plant, botanically known as *Begonia* x *hiemalis*, commercially referred to as an Elatior *Begonia* and hereafter referred to by the name 'KRVALWH02'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant is a naturally-occurring whole plant mutation of *Begonia* x *hiemalis* 'KRVALPI01', disclosed in U.S. Plant Pat. No. 27,005. The new *Begonia* plant was discovered and selected by the Inventor as a single flowering plant from within a population of plants of 'KRVALPI01' in a controlled greenhouse environment in Ermelo, The Netherlands in May, 2016. Asexual reproduction of the new *Begonia* plant by terminal vegetative cuttings taken in a controlled greenhouse environment in Ermelo, The Netherlands since March, 2017 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRVALWH02'. These characteristics in combination distinguish 'KRVALWH02' as a new and distinct *Begonia* plant:

1. Upright to outwardly spreading and mounded plant habit.
2. Moderately vigorous growth habit.
3. Freely branching habit.
4. Dark green-colored leaves.
5. Freely flowering habit.
6. Double-type flowers that are white and yellow in color and held above and beyond the foliar plane.
7. Excellent postproduction longevity.

Plants of the new *Begonia* differ primarily from plants of the mutation parent, 'KRVALPI01', primarily in flower color as plants of 'KRVALPI01' have reddish pink-colored flowers whereas plants of the new *Begonia* have white and yellow-colored flowers.

Plants of the new *Begonia* can be compared to plants of *Begonia* x *hiemalis* 'KRSSUWH01', disclosed in U.S. Plant Pat. No. 23,205. In side-by-side comparisons conducted in Ermelo, The Netherlands, plants of the new *Begonia* differ primarily from plants of 'KRSSUWH01' in the following characteristics:

1. Plants of the new *Begonia* have smaller leaves than plants of 'KRSSUWH01'.
2. Plants of the new *Begonia* have smaller flowers than plants of 'KRSSUWH01'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical plant of 'KRVALWH02' grown in a container.

The photograph on the second sheet are close up views of the upper (right) and lower (left) surfaces of typical leaves and flowers of 'KRVALWH02', and in the center of the photograph is a close-up view of typical flower buds.

DETAILED BOTANICAL DESCRIPTION

The aforementioned photographs and following observations and measurements describe plants grown during the spring and early summer in 12-cm containers in a glass-covered greenhouse in Ermelo, The Netherlands and under cultural practices typical of commercial *Begonia* production. During the production of the plants, day temperatures averaged 20° C. and night temperatures averaged 18° C. Plants were eleven weeks old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRVALWH02'.

Parentage: Naturally-occurring whole plant mutation of *Begonia* x *hiemalis* 'KRVALPI01', disclosed in U.S. Plant Pat. No. 27,005.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Upright to outwardly spreading and mounded plant habit; overall plant shape, broadly obovate.

*Growth habit*.—Moderately vigorous growth habit and moderate growth rate; suitable for 12-cm and larger containers; under optimal environmental and cultural conditions, usually about nine weeks are required to produce proportional plants in 12-cm containers.

*Branching habit*.—Freely branching with about three primary branches each with about two secondary branches developing per plant.

*Plant height, soil level to top of foliar plane*.—About 27 cm.

*Plant height, soil level to top of floral plane*.—About 31.8 cm.

*Plant width*.—About 41.8 cm.

*Lateral branches*.—Length: About 14 cm. Diameter: About 8.5 mm to 9 mm. Internode length: About 3.3 cm. Strength: Moderately strong. Aspect: About 40° from vertical. Texture and luster: Sparsely pubescent; glossy. Color, developing: Close to 144A. Color, developed: Close to between 144A and 146C. Lenticels: Density: Sparse to medium density. Length: About 3 mm. Diameter: About 0.5 mm. Shape: Linear. Color: Close to 145B.

*Leaves*.—Arrangement: Alternate, simple. Length: About 13.8 cm. Width: About 10.1 cm. Shape: Broadly ovate, asymmetrical. Apex: Acute. Base: Hastate with cordate tendencies; lobes slightly imbricate. Margin: Shallowly serrate to dentate; coarsely undulate. Texture and luster, upper surface: Smooth, glabrous; velvety; slightly glossy. Texture and luster, lower surface: Smooth, glabrous; moderately glossy. Venation pattern: Laciniate. Color: Developing leaves, upper surface: Close to 141A. Developing leaves, lower surface: Close to 147B. Fully expanded leaves, upper surface: Darker than between 139A and N189A; venation, close to 143A. Fully expanded leaves, lower surface: Close to between 147B and 191A tinged with close to 182B; venation, close to 146C. Petioles: Length: About 6.2 cm. Diameter: About 5.5 mm. Strength: Low, flexible. Texture and luster, upper and lower surfaces: Sparsely pubescent; moderately glossy. Color, upper surface: Close to 146C tinged with close to 152B; distally, small spot, close to 181B. Color, lower surface: Close to 146C tinged with close to 152B. Stipules: Length: About 9 mm. Width: About 1 cm. Shape: Broadly ovate. Apex: Acute. Base: Broadly cuneate. Margin: Irregularly ciliate. Texture and luster, upper and lower surfaces: Smooth, glabrous; moderately glossy. Color, upper and lower surfaces: Close to 145B.

Flower description:

*Flower appearance and flowering habit*.—Double-type rotate flowers with four, occasionally six, tepals and numerous tepaloids; flowers arranged in axillary compound cymes; freely flowering habit with typically about nine flowers per cyme and about 270 flowers and flower buds developing per plant; many cymes in flower simultaneously; flowers positioned above and beyond the foliar plane and face upright to outwardly; only male flower development has been observed to date on plants of the new *Begonia*.

*Natural flowering season*.—Plants begin flowering about five weeks after planting; plants will flower year round regardless of nyctoperiod, however plants flower earlier and more abundantly from spring into the autumn in The Netherlands.

*Postproduction longevity*.—Individual flowers last about ten days on the plant; flowers not persistent; excellent postproduction longevity, plants maintain good substance for about 40 days in an interior environment.

*Fragrance*.—None detected.

*Inflorescence height*.—About 9.1 cm.

*Inflorescence diameter*.—About 11.1 cm.

*Flowers*.—Shape: Rotate, double-type. Diameter: About 5.6 cm by 5.6 cm. Depth (height): About 1.8 cm.

*Flower buds*.—Length: About 1.6 cm. Diameter: About 0.6 cm to 1.4 cm. Shape: Broadly obovate, flattened. Texture and luster: Glabrous; slightly velvety; matte. Color: Close to between 145D and 150D; towards the base, close to 145B.

*Tepals*.—Quantity and arrangement per flower: Usually about four, occasionally six, per flower arranged in two whorls. Length, lower tepals: About 3.3 cm. Width, lower tepals: About 3.6 cm. Length, upper tepals: About 2.5 cm. Width, upper tepals: About 2.2 cm. Shape, all tepals: Broadly obovate to nearly orbicular. Apex, all tepals: Rounded. Base, all tepals: Reniform. Margin, all tepals: Entire; not undulate. Texture and luster, upper and lower surfaces, all tepals: Smooth, glabrous; moderately velvety; matte. Color, lower tepals: When opening, upper and lower surfaces: Close to between 145D and 150D; towards the base, close to 145C. Fully opened, upper surface: Close to 155C; towards the margins and apex, close to 145C; venation, close to 145C; color does not change with development. Fully opened, lower surface: Close to 157C; towards the margins and apex, close to 145C; venation, close to 145C; color does not change with development. Color, upper tepals: When opening, upper surface: Close to 150D and 4C to 4D. When opening, lower surface: Close to 150D to lighter than 150D. Fully opened, upper surface: Close to NN155B; towards the margins and apex, close to 145D; venation, close to 145C; color does not change with development. Fully opened, lower surface: Close to NN155C; towards the margins and apex, close to 145C; venation, close to 145C; color does not change with development.

*Tepaloids*.—Quantity and arrangement per flower: Typically about 22 to 38 per flower clustered at the center of the flower. Length: About 0.9 cm to 2 cm. Width: About 0.5 cm to 1.3 cm. Shape: Obovate. Apex: Obtuse. Base: Attenuate. Margin: Entire; not undulate. Texture and luster, upper and lower surfaces: Smooth, glabrous; moderately velvety; matte. Color: When opening, upper surface: Close to 154C to 154D. When opening, lower surface: Close to 150D. Fully opened, upper surface: Close to NN155C; towards the base, close to 4C; venation, close to 154C; color does not change with development. Fully opened, lower surface: Close to NN155B; towards the base, close to 4C; venation, close to 154C; color does not change with development.

*Peduncles*.—Length: About 6.5 cm. Diameter: About 4 mm to 5 mm. Strength: Moderately strong. Aspect: About 27.5° from lateral branch axis. Texture and luster: Smooth, glabrous; moderately glossy. Color: Close to 144A.

*Pedicels*.—Length: About 2.5 cm. Diameter: About 2 mm. Strength: Moderately strong. Aspect: About 20° from peduncle axis. Texture and luster: Smooth, glabrous; glossy. Color: Close to 144B.

*Flower bracts*.—Quantity per flower: Two. Length: About 1.5 cm. Width: About 1.4 cm. Shape: Broadly ovate. Apex: Broadly acute. Base: Broadly cuneate. Margin: Ciliate. Texture and luster, upper and lower surfaces: Smooth, glabrous; slightly glossy. Color, upper and lower surfaces: Close to 144B; towards the base, close to 144A; venation, close to 143A to 143B.

*Reproductive organs*.—Stamens are mostly transformed into tepaloids; flowers are sterile. Female flower development has not been observed on plants of the new *Begonia* to date; no seed nor fruit production has been observed to date.

Disease & pest resistance: Resistance to pathogens and pests common to *Begonia* plants has not been observed on plants of the new *Begonia* to date.

Temperature tolerance: Plants of the new *Begonia* have been observed to tolerate high temperatures of about 35° C. and to be suitable for USDA Hardiness Zones 10 to 12.

It is claimed:

1. A new and distinct *Begonia* plant named 'KRVALWH02' as illustrated and described.

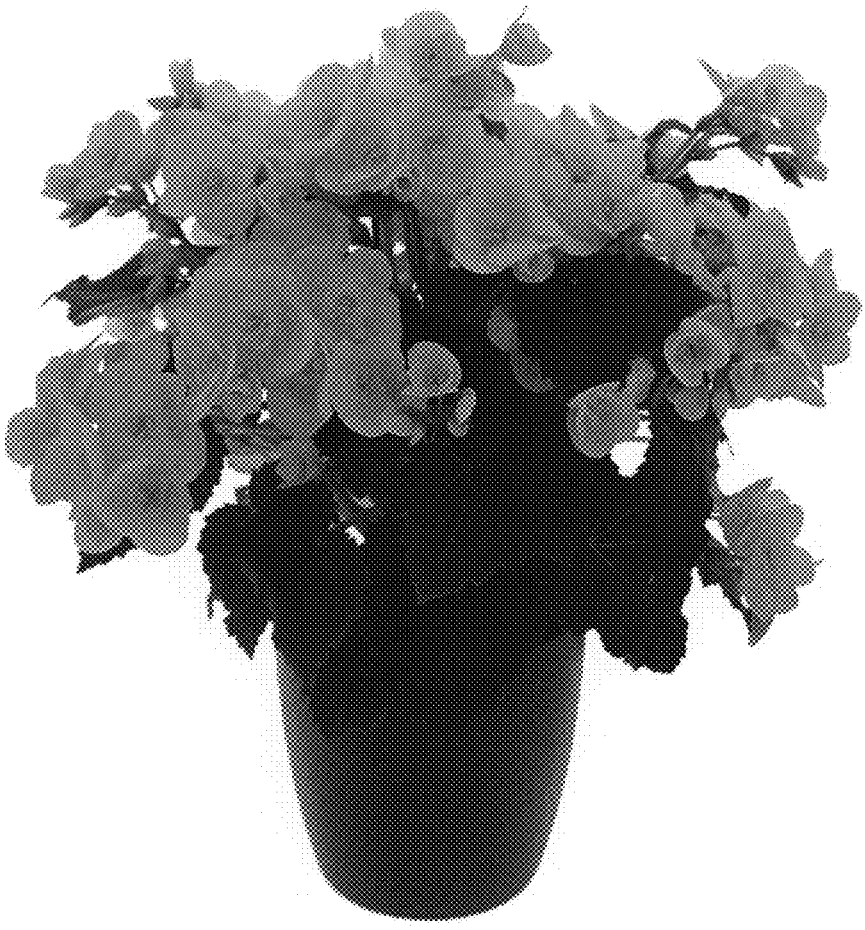

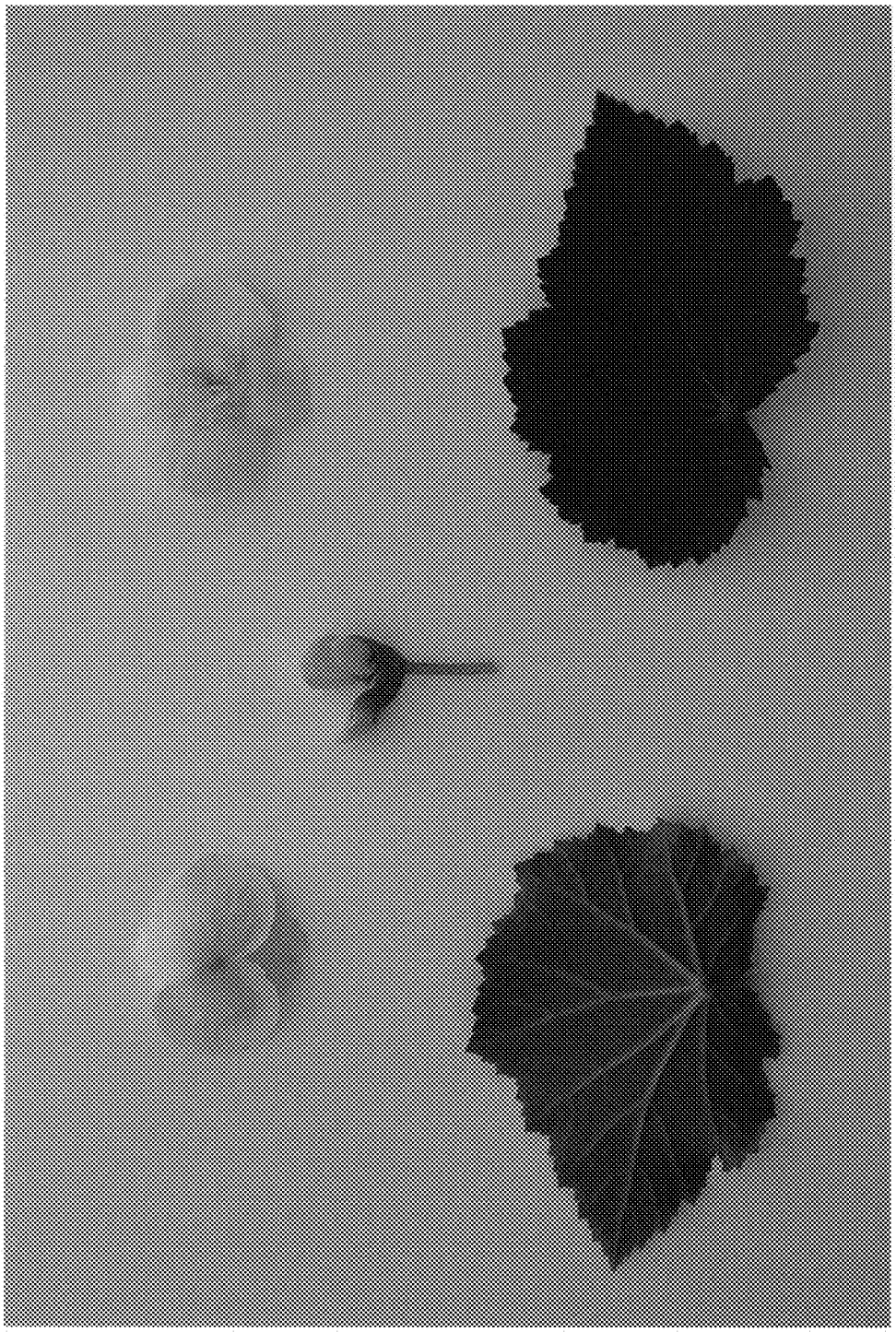

* * * * *